United States Patent [19]
Grandics et al.

[11] Patent Number: 5,571,720
[45] Date of Patent: Nov. 5, 1996

[54] INTEGRATED CELL CULTURE PROTEIN PURIFICATION SYSTEM FOR THE AUTOMATED PRODUCTION AND PURIFICATION OF PROTEINS

[76] Inventors: Peter Grandics; Susan Szathmary, both of P.O. Box 1924, Arcadia, Calif. 91006

[21] Appl. No.: 238,807

[22] Filed: May 6, 1994

Related U.S. Application Data

[63] Continuation of Ser. No. 35,909, Mar. 23, 1992, abandoned, which is a continuation of Ser. No. 389,606, Aug. 4, 1989, abandoned.

[51] Int. Cl.$^6$ .................................................. C12M 3/04
[52] U.S. Cl. ...................... 435/286.1; 435/803; 435/813; 435/70.21; 435/286.6; 435/287.2; 435/297.1; 435/297.4; 435/299.1; 210/679; 210/194; 210/282
[58] Field of Search .................................... 435/287, 284, 435/286, 285, 311, 803, 813; 210/679, 194, 196, 260, 282

[56] References Cited

U.S. PATENT DOCUMENTS

| | | | |
|---|---|---|---|
| 3,328,262 | 6/1967 | Lindblom et al. | 435/813 |
| 3,338,792 | 8/1967 | Patton et al. | 435/813 |
| 3,767,534 | 10/1973 | Miura | 435/813 |
| 3,883,393 | 5/1975 | Knazek et al. | 435/285 |
| 3,887,432 | 6/1975 | Cawthorne | 435/813 |
| 3,941,662 | 3/1976 | Munder et al. | 435/284 |
| 4,033,825 | 7/1977 | Haddad et al. | 195/127 |
| 4,206,285 | 6/1980 | Poulsen et al. | 435/813 |
| 4,264,449 | 4/1981 | Dodd | 210/656 |
| 4,338,399 | 7/1982 | Weil et al. | 435/813 |
| 4,425,433 | 1/1984 | Neves | 435/813 |
| 4,490,290 | 12/1984 | Gani et al. | 435/68 |
| 4,537,860 | 8/1985 | Tolbert et al. | 435/240 |
| 4,722,902 | 2/1988 | Harm et al. | 435/284 |
| 4,889,812 | 12/1989 | Guinn et al. | 435/285 |
| 4,948,736 | 8/1990 | Kobayashi et al. | 435/813 |
| 5,026,828 | 6/1991 | Yamazaki | 530/414 |

FOREIGN PATENT DOCUMENTS

| | | |
|---|---|---|
| 46915 | 3/1982 | European Pat. Off. . |
| 0046915 | 10/1982 | European Pat. Off. . |
| 0201086 | 12/1986 | European Pat. Off. . |

*Primary Examiner*—N. Bhat
*Attorney, Agent, or Firm*—Merchant, Gould, Smith, Edell, Welter & Schmidt

[57] ABSTRACT

An integrated cell culture-protein purification system has been developed for the continuous, automated production of pure cell culture protein products. The instrument comprises a bioreactor subunit having a hollow fiber bioreactor to culture and maintain cells which secrete the desired product into the cell culture medium. The culture medium is circulated through a purification cartridge which adsorbs the desired product. The system is capable of continuously removing the product from the culture medium by immunoaffinity adsorption and pure product is then recovered. The product can also be recovered automatically in a discontinuous operation from the spent culture medium by either affinity, ion exchange, or hydrophobic purification techniques. The integrated system allows continuous production of high-quality, pure proteins from cell culture.

46 Claims, 2 Drawing Sheets

INTEGRATED CELL CULTURE PROTEIN PURIFICATION SYSTEM FOR THE AUTOMATED PRODUCTION AND PURIFICATION OF PROTEINS

This is a continuation of application Ser. No. 08/035,909, filed Mar. 23, 1993, which was abandoned upon the filing hereof, which is a continuation of application Ser. No. 07/389,606, filed on Aug. 4, 1989, now abandoned.

BACKGROUND

Complex proteins are increasingly used in research, diagnostics and therapeutics. Many of these proteins can only be produced in appropriate eucaryotic cells. With the advent of hybridoma technology and other progress in genetic engineering of eucaryotic cells, mammalian or yeast cell lines are becoming the method of choice for producing complex proteins on a large scale.

The secreted product needs to be purified from the cell culture medium. Most mammalian cells require serum which contains a diverse mixture of proteins, many of which are present at high concentrations. Even in serum-free media systems, numerous other proteins are secreted from the cells. For most of the applications the final product has to meet high levels of purity and activity.

The successful production of these proteins depends largely on the development of fast and efficient methods of purification. Typically, the purification constitutes the major cost (up to 80% of the total cost) in these processes. The large scale use of these protein products is hindered because of the high cost.

There is an urgent need for processes to produce proteins in a simple and economical way. Significant cost reduction in the production of protein biologics could be realized if the purification Would be integrated with cell culture into a fully automated system. In addition, the product quality is also expected to improve because the secreted protein is continuously removed from the culture medium in which the product is exposed to catabolic enzymes. Protein identity is an important issue for protein biotherapeutics, i.e. the final product should be free of degraded or other aberrant protein molecules. The integration requires that the presence of the purification unit in the cell culture system would not affect the conditions of cell culture. Therefore, highly-specific purification methods like affinity/immunoaffinity chromatography is needed to make the integration of cell culture and purification feasible for the continuous purification of secreted product.

Progress in cell culture technology has led to the development of membrane bioreactors for growing eucaryotic, such as mammalian cells within well-defined compartments. Cells grown inside low nonspecific adsorption flat sheet or hollow fiber membranes in thin (200–400 µm) layers are continuously perfused with nutrients and grow to cell densities previously unattainable by the stationary, stirred tank or airlift-type fermentors. Nutrient deprivation or shear sensitivity issues are minimized by this technology. This allows high cell viability in the bioreactor and minimize DNA contamination of the product. The microfiltration membrane eliminates the opportunity of bacterial contamination of the bioreactor. The cells are grown at tissue density with high production rates surpassing the production capacity of conventional bioreactors. After populating the available compartment space, the cells reach a growth-arrested state in which most of their energy is directed towards production. This configuration allows the highest production capacity per unit volume of bioreactor space.

Another important aspect of the integration is the availability of appropriate protein separation technologies. Current protein purification technologies require significant improvement in order to realize the potentials of the integration concept. A major obstacle is that the interaction of the cell culture medium with the protein separation material (chromatography resin) may change the composition of the medium which can be detrimental to the cells in culture. Chromatography media like ion exchange or hydrophobic matrices can drastically change the culture medium composition and thus are unsuitable for an integrated instrument if continuous removal of the product is desired. Biospecific, affinity separation is the only method offering the least interference with cell culture. However, current affinity technologies have serious shortcomings which have prevented them from being incorporated into an integrated system.

The integration of cell culture with continuous purification of secreted product without jeopardizing the cell culture by introducing potentially toxic chemicals and bacterial/vital contamination necessitates the development of a stable, nontoxic, chemically inert, sterilizable activated affinity chromatography resin. Current activated affinity matrices cannot be incorporated into the integrated instrument because they do not meet the criteria of being chemically inert, nontoxic, stable, and sterilizable. The most commonly used coupling methods employ reactive electrophilic centers with leaving group displaced by the incoming nucleophilic ligand (protein/antibody). These displacement reactions frequently remain incomplete even after capping the unreacted sites and continue to release leaving groups, many of them are toxic to cells. Conversely, constituents of the culture medium may be covalently attached to the matrix. The affinity resin may leach other toxic molecules, like isocyanate from CNBr-activated matrices, for long periods of time. This is toxic to the cells in the bioreactor. The iramobilization method may also increase the protease sensitivity of immobilized protein (antibody) ligand, an issue which is a problem with the traditional coupling chemistries.

In affinity separations, proteins (antibodies) are frequently used as ligand. In the integrated system, the immunoaffinity chromatography resin must withstand the conditions of cell culture for long periods of time. The warm, highly-oxygenated environment of cell culture medium may diminish the activity of the immunoaffinity column. Many of the cultured mammalian cells, including hybridomas, secrete proteolytic enzymes which may degrade the immobilized antibody ligand. The same applies to dead cells spilling their content into the culture medium. The structure of the support and the method of immobilization also plays an important role in the protease sensitivity of immobilized antibody. The low concentration of secreted proteins in the cell culture medium may also complicate quantitative recovery of the product.

Current immunoaffinity technologies make process automation complicated because of the continuous loss of immunosorbent capacity. This is the result of ligand leaching and inactivation of immobilized antibody for reasons mentioned above. The total cycle life of the immunoadsorbent (5–30 cycles) is usually too short to make this technology suitable for the integration of bioreactor and purification for continuous product recovery. All these issues need to be addressed in order to make affinity chromatography media compatible with mammalian cell culture.

LIST OF REFERENCE NUMERALS

Figure 1:
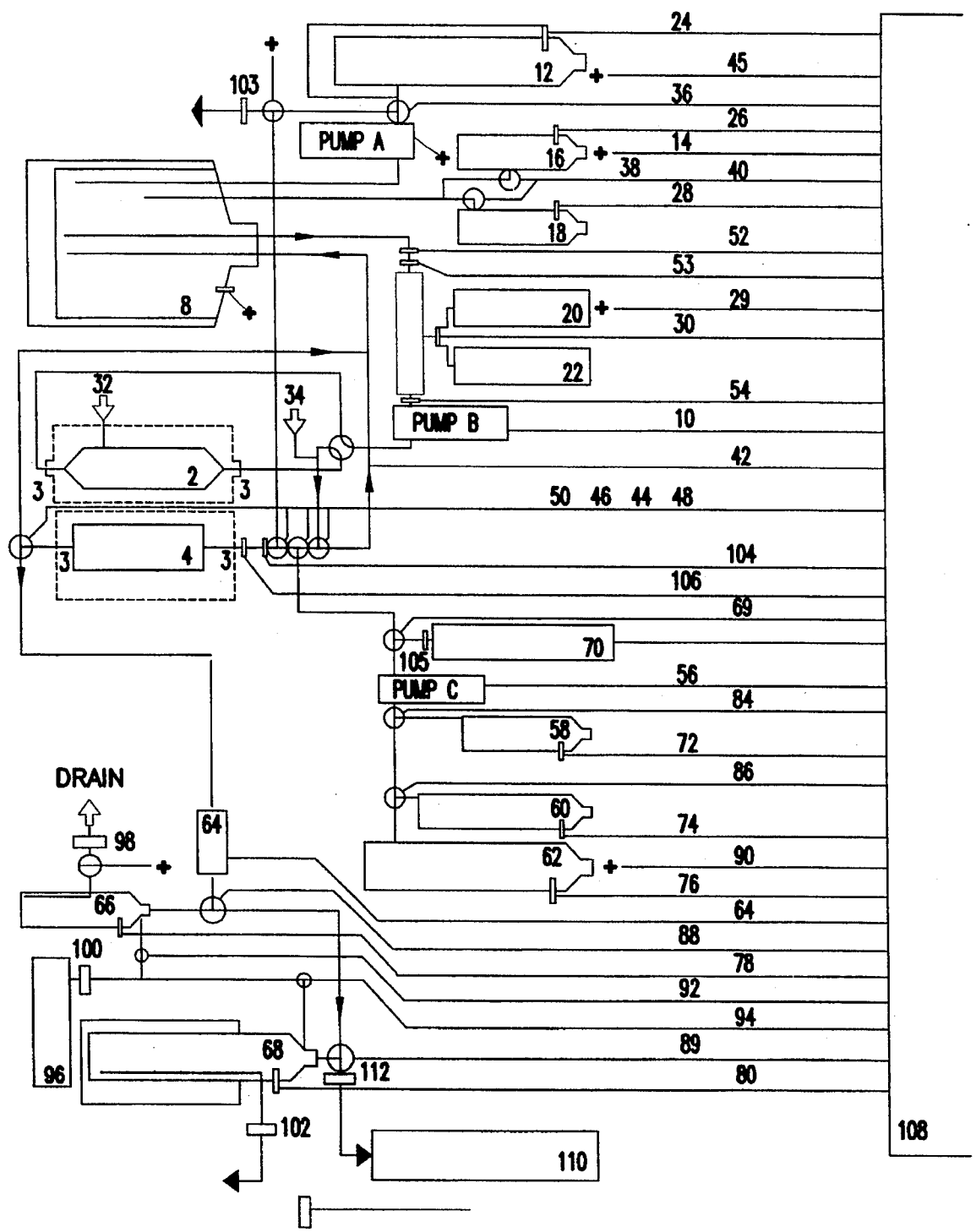
FIG. 1 is the flow diagram of the invention integrated cell culture/purification system.

2 Cell culture unit/bioreactor
4 Purification unit/chromatography cartridge
6 Oxygenator
8 Cell culture medium vessel
10 Pump B
12 Cell culture medium container
14 Pump A
16 Base container
18 Acid container
20 Compressed air source
22 Carbon dioxide source
24, 26, 28 29 Level sensors
30 Gas flow control
32, 34 Injection ports
32 Three-way valve
38, 40 Two-way valves
42 Four-way valve
44, 45, 46, 48, 50 Three-way valves
52 pH probe
53 Temperature probe
54 Dissolved oxygen probe
56 Pump C
58 Culture medium container
60 Wash medium container
62 Elution medium container
64 Flow cell UV monitor
66 Waste fluid container
68 Product vessel
70 Gradient former
72, 74, 76, 78, 80 Level sensors
82, 84, 86, 88, 89 Three-way valves
90 Two-way valve
92, 94 Two-way air valves
96 Compressed air source
98, 100, 102, 103, 105, 112 Sterile filters
104 Pressure sensor
106 Bubble sensor
108 Controller
110 Fraction collector

DESCRIPTION OF THE PREFERRED EMBODIMENT

Cell culture is a versatile technique for producing a variety of complex biomolecules including proteins. The protein of interest is produced and secreted by the cultured cells into the cell culture fluid of which the product is recovered, in many cases, by using complicated, multi-step purification procedures. This frequently results in significant product losses and an increased possibility of generating aberrant protein molecules. We have developed a new integrated instrument which unifies the formerly separate cell culture and protein purification into an integrated, automated operation which significantly reduces the manufacturing cost of high purity cell culture protein products. The product quality is also increased as a result of the integrated production of proteins. The integrated cell culture/purification instrument has two subunits, such as the bioreactor and chromatography subunits (FIG. 1).

In the subject invention, the cell culture unit is a hydrophilic hollow fiber bioreactor (Zymax, Microgon). The 2 bioreactor consists of compact coaxial fibers in a cylindrical housing. The fibers are usually 0.2–1.0 mm in diameter with a pore size of 0.2 micron. The space within the fibers is called intra-capillary space (ICS) and the outside region is designated extra-capillary space (ECS). The cells are detained in ECS whereas ICS has nutrient or culture medium flowing through. The pore size of the fibers is small enough to contain the cells (approx. 10 microns in diameter), but allows exchange of nutrients and proteins across the membrane by diffusion.

The bioreactor environment needs to be carefully controlled because slight changes may lead to decreased productivity or cause cell death. The important parameters to be controlled are temperature, pH, dissolved oxygen and nutrient levels of the culture medium. Mammalian cells are very sensitive to chemical contaminants. A wide variety of substances even at ppm level could be highly toxic to the cells. Under the right culture conditions the cells remain active in the bioreactor for a couple of months or even longer. To maintain the temperature, the system can be equipped with a refrigeration unit to maintain the bioactivity of perishable materials. The refrigeration unit can keep a purified cell culture product at a temperature of from 0° C. to 10° C.

To control bioreactor conditions, probes, such as the 53 temperature probe, 52 pH electrode and 54 dissolved oxygen probe need to be included into the bioreactor loop and linked to the programable 108 controller. A suitable controller may be a microprocessor controlled unit like the Proteus 2000 (Wheaton Scientific Instruments). The 108 controller receives information from the probes and makes appropriate adjustments in the above culture conditions. The pH is adjusted by autotitration of the culture medium from 18 acid or 16 base containers. The temperature is adjusted by warming the medium flask while the dissolved oxygen is changed by a 30 gas flow controller by increasing the air pressure on the 6 oxygenator.

The 6 oxygenator (Microgon) is also of hollow fiber-type containing hydrophobic fibers with a pore size of 0.02 micron; 5% $CO_2$ in air mixture is passed through the oxygenator. The bioreactor loop contains the culture medium supply system which, in the simplest case, is a medium container changed periodically as the medium gets exhausted. In an automated fashion, feeding of cells is accomplished by continuous perfusion (feed and bleed system) by introducing fresh and withdrawing spent medium from the bioreactor loop at a preset rate. This is accomplished by using the 14 reversible pump (Pump A) which first withdraws spent medium from the 12 medium vessel and then replenishes it with fresh medium. The spent medium exits the system through the 45 valve and 103 hollow fiber filter, 0.2 micron, into the drain. Alternatively, the spent medium may be recycled through 45 and 46 valves onto the 4 purification unit for subsequent purification of the product.

The 2 bioreactor and 4 affinity chromatography column is enclosed into plug-in type cartridges which are presterilized and attached to the instrument through 3 snap-in connectors. The cartridges, containing the appropriate chromatography medium, can be sterilized by autoclaving or sodium hydroxide. The chromatography medium can be an affinity medium for covalent attachment of proteins or ligands. The medium can be derivatized with nonproteinaceous molecules or proteins. Among the proteins that can be used to derivatize the medium are antibodies, including light chain specific antibodies or heavy chain specific antibodies. The purification medium can alternatively comprise a protein binding ligand, which can be an antibody of appropriate specificity, an ion exchange group, a hydrophobic group, or an affinity ligand. After each run, the cartridges are discarded. The rest of the instrument can be sterilized in place by using a chemical sterilant, such as 2% to 15% glutaraldehyde (v/v). After the specified time of sterilization, the glutaraldehyde is drained and the whole system is extensively washed with sterile, pyrogen-free deionized water (tissue culture grade) introduced through the connecting port of 70 gradient former. Alternatively, sterilization can be carried out by autoclaving. The bioreactor loop is then filled with culture medium and the 2 bioreactor is inoculated with the cells. The nutrients are delivered to the cells in the 2 bioreactor at a flow rate of 30–150 ml/min by using 10 Pump B.

The bioreactor loop contains 32 and 34 aseptic injection ports. Through 32 port, either medium can be withdrawn from the bioreactor loop or compounds can be introduced into the cell culture medium. Through 34 port, the bioreactor is inoculated with the cells to start operation. The 42 four-way valve and the 48 and 50 three-way valves direct the culture medium on or off the 4 purification unit. The 4 purification unit is not in operation before the cells populate the bioreactor. In the continuous mode of operation, after the sixth day, the 108 controller initiates the product recovery cycles.

The bioreactor was inoculated with $5 \times 10^7$ hybridoma cells. The mouse x mouse hybridoma (HB 57) producing IgG1 monoclonal antibody was grown in RPMI 1640 medium supplemented with antibiotic solution and 10% iron-supplemented calf serum. This hybridoma is a low producer and requires a minimum of 10% serum for optimal growth and antibody production. The culture medium is kept at 37° C. in the bioreactor loop. Cell density and viability were determined by using hemocytometer and Trypan blue staining.

The bioreactor loop interfaces with the purification/chromatography loop through the 4 purification unit which can be an affinity cartridge. The affinity cartridge is a polymeric cylindrical container closed with porous disks at the top and bottom and is filled with a fast flow activated affinity resin, Actigel-ALD Superflow (patent pending) to which an antibody to the desired product is attached. Actigel-ALD Superflow (Sterogene Bioseparations, Inc.) is a stable, nontoxic and sterilizable (autoclavable) activated resin. In this example, an affinity-purified, goat anti-mouse light chain-specific antibody is attached to the resin at a concentration of 1 mg/ml to 10 mg/ml. The immunoaffinity resin has an extremely low content of leachables (<0.1 ppm IgG) and is not toxic to mammalian cells. In the adsorption mode of operation, the culture medium is continuously circulated through the 4 affinity cartridge which adsorbs the monoclonal antibodies, secreted by the hybridomas in the 2 bioreactor, from the culture medium. Periodically, the 4 affinity cartridge is taken off-line from the bioreactor loop by using the 42, 48 and 50 valves and the product recovery cycle is initareal by the 108 controller.

The separation loop is driven by 56 Pump C which delivers the 60 wash-, 62 elution-, and 58 regeneration media in the specified sequence. First, the residues of the tissue culture medium and nonspecifically adsorbed proteins are removed by extensive washing with the 60 wash medium, 0.3M NaCl. This step is followed by the elution of monoclonal antibodies from the 4 affinity column by using 1 bed volume of 62 ActiSep Elution Medium (patent pending) over a period of 30 min. ActiSep (Sterogene Bioseparations, Inc.) is a nondenaturing elution medium allowing 100 or more cycles to be performed on immunoaffinity columns. The eluant retains the binding capacity of the immunoadsorbent during many cycles of operation as well as high bioactivity of the eluted product. Eluted protein peak is monitored by $OD_{280}$ measurement in a flow cell UV photometer and the protein peak is integrated to quantitate eluted antibody. The product is collected into a 68 refrigerated storage bottle while the washes are collected into a separate 66 waste bottle. When all the elution medium is recovered from the affinity column, another wash with 0.3M NaCl is initiated to remove traces of the eluant. This is followed by a wash with the 58 cell culture medium (RPMI 1640) to equilibrate the column for the subsequent product adsorption cycle.

The 66 waste and 68 product bottles are emptied by 96 compressed air introduced through 100 sterile filter. The air flow is directed by the 92 and 94 valves into the respective bottles. The waste exits the system into the drain through 98 sterile filter, 0.2 micron pore size, and 90 two-way valve. The product exits the system through the 102 sterile filter, 0.2 μm pore size, into a collection flask from which it is collected by the operator.

The emptying of the waste and product vessels is initiated by the 108 controller receiving signals from the 78 and 80 level sensors. The 72, 74, and 76 level sensors monitor fluid levels in the 56, 58, 60 and 62 buffer vessels. The 108 controller issues warning signals to the operator to fill empty bottles. Until the buffer/medium bottles are replenished, no further product adsorption and elution cycles are initiated by the controller. The separation loop contains additional safety controls, such as 104 pressure and 106 bubble sensors to protect the 4 purification unit from pressure build-up or from running dry.

Figure 2:
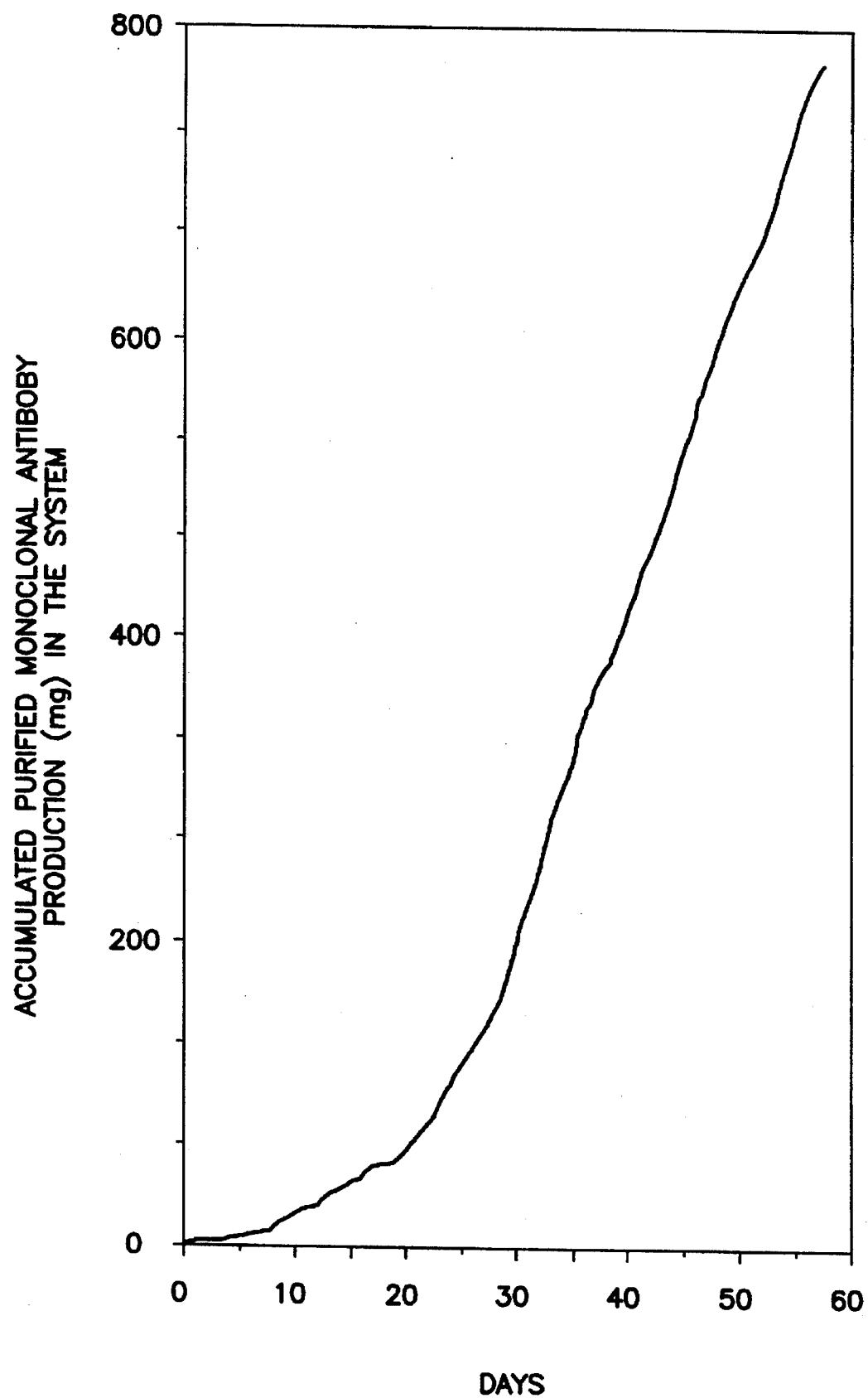
FIG. 2 is the accumulated production of purified monoclonal antibody in the integrated cell culture/purification system.

The accumulated antibody production of the system is shown in FIG. 2. After an approximately 1 week lag period, the antibody level has exceeded 10 ug/ml in the culture medium and continuous separation of the product has commenced. Over a period of 60 days, an accumulated 800 mg of affinity-purified monoclonal antibody was recovered from the integrated system. The purity of antibody was tested by SDS-polyacrylamide gel electrophoresis. Single heavy and light chains were observed indicating a protein purity of approximately 99%. Importantly, no sign of degradation of antibody is found which underscores the significance of the integration concept, i.e., the continuous removal of the product from the culture fluid in which the antibody is exposed to proteolytic enzymes deriving from the serum and dead cells. Therefore, besides improving the economy of the process, the product quality is also improved.

If proteins other than antibodies need to be purified in a continuous fashion from the cell culture medium, the operator has to immobilize his antibody to the product to 4 purification unit which, in this case, contains Actigel-ALD Superflow activated support. The antibody mixed with the coupling reagent is injected into 4 cartridge through 32 sterile port and the reaction is allowed to take place for 6 h (Sterogene Bioseparations, Inc., Actigel-ALD Superflow Technical Bulletin). Unbound protein is removed by washing with 60 wash medium and then with 58 cell culture medium to prepare the cartridge for the product adsorption cycle.

The major advantages of the continuous removal of the product from the cell culture medium are as follows:

1. Significant improvement in product quality. The immediate removal of the protein product from the cell culture minimizes the chances of product degradation.

2. Significant reduction in process development time. The cell culture process development can be minimized because there is no need to adapt the cells to low serum or defined media. Serum-containing culture medium can be used because the affinity purification of the product eliminates the concern as to the presence of serum proteins. The generic purification method, immunoaffinity chromatography significantly simplifies product recovery.

3. Significant reduction in the manufacturing cost of cell culture products. The cost of cell culture can be reduced by a factor of 5–10 because there is no need to use defined media or expensive fetal bovine serum. The specificity of immunoaffinity separation eliminates contaminants of bovine serum origin; therefore there is no need for low IgG fetal serum. The cost of protein purification is also reduced by a factor of 10–15 because of the automation and long-term utilization of the immunoadsorbent.

Because of these advantages, continuous product recovery is strongly preferred. However, in certain cases when the characteristics of the product justifies it, discontinuous product recovery by other methods may be used. If the secreted product is resistant to proteolysis/degradation and the protein concentration in the cell culture medium is low, i.e. a low protein, defined medium is used, the product may be recovered from the spent culture medium in a discontinuous fashion as follows:

1. The spent medium, withdrawn from the 8 medium vessel by 14 reversible pump (Pump A) is directed by 45 and 46 three-way valves onto 4 separation unit/chromatography cartridge which may contain an ion exchange-, hydrophobic interaction(HIC)-, or affinity chromatography medium. In the event, if ion exchange chromatography is used, the column may contain e.g. a DEAE-type medium, equilibrated with 50 mM Tris, pH 8.0, delivered from vessel 62. Vessel 60 is filled with 50 mM Tris, pH 8.0, 1M NaCl regeneration buffer. Vessel 58 contains a 2 mM Tris, pH 8.0 dilution buffer delivered by 56 pump (Pump C) to 4 chromatography cartridge along with the culture medium to lower the ionic strength of the cell culture medium. The appropriately diluted cell culture medium is applied to 4 ion exchange cartridge and washed with the 62 equilibration buffer. The desired product is then eluted by a gradient elution, generated by 70 gradient former from 0% (equilibration buffer) to 100% (end buffer, such as 50 mM Tris, pH 8.0, 0.3M NaCl). The eluted product is measured at 280 nm in the 64 flow cell UV. monitor. The protein concentration is calculated by integrating the elution peak. Through the 89 three-way valve and 112 sterile filter, 0.2 micron pore size, eluted product exits the system into the 110 fraction collector. The column is regenerated for the next adsorption cycle by washing with the regeneration buffer (vessel 60) and equilibration buffer (vessel 62).

2. In the event if HIC is preferred for the purification of the product, the 4 cartridge contains an appropriate medium, such as phenyl-, octyl-, butyl-, hexyl-, isopentyl-liganded or other HIC media. The 4 HIC cartridge is equilibrated with the binding salt by using 70 gradient former. The cell culture medium is then applied as described for the ion exchange chromatography separations. The binding salt is applied through 70 gradient former at the appropriate ratio. Unbound materials are washed with the binding salt solution and then product is recovered by applying a low salt buffer or a reverse salt gradient onto the 4 cartridge through the 70 gradient former. Through the 89 three-way valve and 112 sterile filter, 0.2 micron pore size, eluted product exits the system into the 110 fraction collector. The column is regenerated for the next adsorption cycle by washing with the regeneration buffer (vessel 60) and equilibration buffer (70 gradient former).

3. In the discontinuous product recovery mode, affinity chromatography may also be used. For example, 4 purification unit may contain immobilized Protein A or Protein G capable of binding antibodies. The culture medium is applied to the 4 affinity cartridge in accord with paragraph 1. A wash fluid, e.g. 50 mM Tris, pH 8.0, 0.15M NaCl is then applied from vessel 60 and directed to 66 waste bottle. The length of the wash is determined by monitoring $OD_{280}$ in the waste fluid. The bound antibody is then eluted by delivering one column volume of ActiSep Elution Medium from vessel 62 over a period of 30 min onto the 4 cartridge. If pH gradient elution is desired, 70 gradient former can generate the required pH gradient profile. Through the 89 three-way valve and 112 sterile filter, 0.2 micron pore size, eluted product exits the system into the 110 fraction collector. The column is regenerated for the next adsorption cycle by washing with the equilibration buffer (60 vessel).

Besides operating as a cell culture/purification system, the instrument can also operate as a stand alone cell culture unit to culture and characterize cell lines. This is important if a new cell line need to be developed and culture conditions optimized for the production of a particular protein.

When the cell culture conditions are optimized, an optimal purification strategy can be developed for the product which may be a continuous immunoaffinity method or a discontinuous conventional, ion exchange or HIC purification or some other affinity methods. This decision is made based on the cell culture conditions and the sensitivity of the product to degradation as well as the intended use of the protein. For therapeutic applications where the product identity is a major issue, continuous product purification is desirable as this method protects the product against degradation. If the product is more resistant to degradation and protein identity is of a lesser problem, discontinuous product purification may be suitable.

If purification of the secreted product is not desired, the separation loop can be utilized, independently from the bioreactor loop, for the purification of proteins like antibodies from biological fluids, such as serum or ascitic fluid. For the purification, ion exchange, HIC or affinity methods may be used following the description of paragraphs 1, 2 and 3. In general, the sample to be purified is applied to 4 purification unit from 58 vessel. This is followed by the application of the wash fluid from vessel 60 and then elution is initiated either by applying a single eluant from vessel 62 or using gradient elution through 70 gradient former.

Polishing purification of the product, obtained by continuous, immunoaffinity purification of secreted protein can also be accomplished as described in paragraphs 1, 2 and 3. These features allow the utilization of the instrument for the integrated production and purification of secreted product from cell culture with the built-in flexibility of applying a number of different purification strategies for product recovery with the objective of obtaining pure protein product while minimizing changes in product identity.

We claim:

1. An integrated cell culture and purification system for producing a purified cell culture product, consisting essentially of:

a. a cell culture subunit for culturing cells;

b. a purification subunit linked to the cell culture subunit adapted to remove said product from a culture fluid in which the cells are cultured by purification means comprising a solid-phase medium; and c. means for circulating said culture fluid from said cell culture subunit to said purification subunit, said cell culture subunit, said purification subunit and said means for circulating being integrated in a single unit and contained in a sterile environment to purify said product in a sterile environment without removing said culture fluid from said integrated cell culture and purification system; said purification subunit separating said product from other molecules of substantially equivalent molecular weight by specific interactions and removing one immunoglobulin molecule from another immunoglobulin molecule of different binding specificity.

2. The system of claim 1, wherein said system further includes means for discontinuing said circulation of cell culture fluid through said purification subunit and eluting purified product from said purification subunit.

3. The system of claim 1, wherein said cells in said cell culture subunit are separated from said purification subunit by a porous membrane.

4. The system of claim 1, wherein said cell culture system comprises a bioreactor for permitting contact between said cells and said culture fluid while preventing said cells from leaving said bioreactor when said culture fluid is circulated to said purification subunit.

5. The system of claim 4, wherein said bioreactor is a hollow fiber bioreactor, and said cells are retained by hollow fibers of said bioreactor.

6. The system of claim 1, wherein said cell culture subunit further comprises an oxygenator for supplying oxygen to said cells by oxygenating said culture fluid.

7. The system of claim 1, wherein said purification subunit comprises a self-contained plug-in cartridge adapted for ready attachment to or removal from said system.

8. The system of claim 7, wherein said cartridge comprises a solid phase affinity medium for covalent attachment of proteins or ligands.

9. The system of claim 8, wherein said solid phase medium comprises aldehyde functional groups.

10. The system of claim 8, wherein said solid phase affinity medium is sterilizable by autoclaving or sodium hydroxide.

11. The system of claim 8, wherein said solid phase affinity medium is derivatized with nonproteinaceous molecules.

12. The system of claim 8, wherein said solid phase affinity medium is derivatized with proteins.

13. The system of claim 8, wherein said solid phase affinity medium is derivatized with antibodies.

14. The system of claim 8, wherein said solid phase affinity medium is derivatized with light chain specific antibodies.

15. The system of claim 8, wherein said solid phase affinity medium is derivatized with heavy chain specific antibodies.

16. The system of claim 8, wherein said solid phase medium is derivatized with antibodies at a concentration of 1 mg/ml to 10 mg/ml resin.

17. The system of claim 12, wherein said proteins with which said solid phase affinity medium is derivatized are coupled to said solid phase affinity medium in said purification cartridge by injecting said proteins onto said cartridge through a sterile port.

18. The system of claim 1, wherein said bioreactor subunit comprises a self-contained plug-in type bioreactor cartridge adapted for easy attachment to or removal from said system.

19. The system of claim 1, wherein said bioreactor subunit comprises a thermostated culture medium vessel to maintain optimal temperature for cell culture.

20. The system of claim 1, wherein said bioreactor subunit comprises a gas flow regulator to provide adequate oxygenation for the cell culture.

21. The system of claim 1, further comprising a refrigeration unit to maintain the bioactivity of perishable materials.

22. The system of claim 21, wherein said refrigeration unit maintains said purified cell culture product at 0°–10° C.

23. The system of claim 1, wherein said system is sterilizable prior to starting operations.

24. The system of claim 23, wherein said system is autoclavable.

25. The system of claim 23, wherein said system is sterilizable by using a chemical sterilant.

26. The system of claim 25, wherein said system is sterilizable by glutaraldehyde.

27. The system of claim 26, wherein said system is sterilizable by glutaraldehyde at a concentration range of 2–15% (v/v).

28. The system of claim 23, wherein said bioreactor and purification cartridges are presterilized before connection to the system.

29. The system of claim 1, wherein said purification cartridge comprises a protein binding ligand.

30. The system of claim 29, wherein said protein binding ligand is an antibody.

31. The system of claim 29, wherein said protein binding ligand is an affinity ligand.

32. A process for recovering a product secreted by cells growing in a cell culture and purification system, comprising the steps of:

a. culturing cells grown in a cell culture and purification system, the system consisting essentially of:
   (i) a cell culture subunit for culturing cells;
   (ii) a purification subunit linked to said cell culture subunit adapted to remove said product from a culture fluid in which the cells are cultured by purification means comprising a solid-phase medium, said purification subunit comprising a self-contained plug-in cartridge adapted for ready attachment to or removal from said system; and
   (iii) means for circulating said culture fluid from said cell culture subunit to said purification subunit; said cell culture subunit, said purification subunit, and said means for circulating being integrated in a single unit and contained in a sterile environment to purify said product in a sterile environment without removing said culture fluid from said integrated cell culture and purification system;

b. extensively washing the cartridge with a wash buffer to remove contaminating protein;

c. eluting the cartridge with amount elution medium to obtain purified product; and d. regenerating the cartridge with consecutive washes with wash buffer and subculture medium for a subsequent absorption cycle; the process separating said product from other molecules of substantially equivalent molecular weight by specific affinity interactions and removing one immunoglobulin molecule from another immunoglobulin molecule of different binding specificity.

33. The process of claim 32, further comprising the step of quantitating said purified protein by ultra-violet spectrophotometry and subsequently integrating the protein peak.

34. The process of claim 32 wherein the solid-phase medium is substantially free of leachables toxic to the cells being cultured.

35. The method of claim 32 wherein the solid-phase medium provides at least one month of continuous cell culture without significant toxic effects on the cells being cultured.

36. A discontinuous process for recovering and purifying a product secreted by cells grown in a cell culture and purification system, comprising the steps of:
   a. culturing cells grown in a cell culture and purification system, the system consisting essentially of:
      (i) a cell culture subunit for culturing cells;
      (ii) a purification subunit linked to said cell culture subunit adapted to remove said product from a culture fluid in which the cells are cultured by purification means comprising a solid-phase medium, said purification subunit comprising a self-contained plug-in cartridge adapted for ready attachment to or removal from said system; and
      (iii) means for circulating said culture fluid from said cell culture subunit to said purification subunit; said cell culture subunit, said purification subunit, and said means for circulating being integrated in a single unit and contained in a sterile environment to purify said product in a sterile environment without removing said culture fluid from said integrated cell culture and purification system;
   b. withdrawing spent culture medium from said culture subunit by using a pump;
   c. directing said spent medium onto said purification cartridge comprising an absorption medium;
   d. removing unbound cell culture medium constituents by a wash process; and
   e. eluting bound products from said purification cartridge to obtain purified product; said purification means separating said product from other molecules of substantially equivalent molecular weight by specific affinity interactions and removing one immunogobulin molecule from another immunoglobulin molecule of different binding specificity.

37. The process of claim 36, wherein said step of eluting bound product involves changes to the ionic strength and/or the pH within the purification cartridge.

38. The process of claim 36 wherein the solid-phase medium is substantially free of leachables toxic to the cells being cultured.

39. The process of claim 36 wherein the solid-phase medium provides at least one month of continuous cell culture without significant toxic effects on the cells being cultured.

40. An integrated cell culture and purification system for producing a purified cell culture product, consisting essentially of:
   a. a cell culture subunit for culturing cells;
   b. a purification subunit linked to the cell culture subunit adapted to remove said product from a culture fluid in which the cells are cultured by purification means comprising a solid-phase medium; and
   c. means for circulating said culture fluid from said cell culture subunit to said purification subunit; said cell culture subunit, said purification subunit, and said means for circulating being integrated in a single unit and contained in a sterile environment to purify said product in a sterile environment without removing said culture fluid from said integrated cell culture and purification system; said purification subunit separating said product from other molecules of substantial molecular weight by a chromatographic method selected from ion exchange and hydrophobic interaction chromatography and removing one immunoglobulin molecule from another immunoglobulin molecule of different binding specificity.

41. A process for recovering a product secreted by cells growing in a cell culture and purification system, comprising the steps of:
   a. culturing cells grown in cell culture and protein purification system, the system consisting essentially of:
      (i) a cell culture subunit for culturing cells;
      (ii) a purification subunit linked to said cell culture subunit adapted to remove said product from a culture fluid in which the cells are cultured by purification means comprising a solid-phase medium, said purification subunit comprising a self-contained plug-in cartridge adapted for ready attachment to or removal from said system; and
      (iii) means for circulating said culture fluid from said cell culture subunit to said purification subunit; said cell culture subunit, said purification subunit, and said means for circulating being integrated in a single unit and contained in a sterile environment to purify said product in a sterile environment without removing said culture fluid from said integrated cell culture and purification system;
   b. extensively washing the cartridge with a wash buffer to remove contaminating protein;
   c. eluting the cartridge with a mild elution buffer to obtain purified product; and
   d. regenerating the cartridge with consecutive washes with wash buffer and subculture medium for a subsequent absorption cycle; the process separating said product from other molecules of substantially equivalent molecular weight by a chromatographic method selected from ion exchange and hydrophobic interaction chromatography and removing one immunoglobulin molecule from another immunoglobulin molecule of different binding specificity.

42. A discontinuous process for recovering and purifying a product secreted by cells growing in a cell culture and purification system, comprising the steps of:
   a. culturing cells grown on a cell culture and purification system, the system consisting essentially of:
      (i) a cell culture subunit for culturing cells;
      (ii) a purification subunit linked to said cell culture subunit adapted to remove said product from a culture fluid in which the cells are cultured by purification means comprising a solid-phase medium, said purification subunit comprising a self-contained plug-in cartridge adapted for ready attachment to or removal from said system; and
      (iii) means for circulating said culture fluid from said cell culture subunit to said purification subunit; said cell culture subunit, said purification subunit, and said means for circulating being integrated in a single unit and contained in a sterile environment to purify said product in a sterile environment without removing said culture fluid from said integrated cell culture and purification system;
   b. withdrawing spent culture medium from said culture subunit by using a pump;

c. directing said spent medium onto said purification cartridge comprising an absorption medium;

d. removing an unbound cell culture medium constituent by a wash process;

e. eluting bound product from said purification cartridge to obtain purified product; said purification means separating said product from other molecules of substantially equivalent molecular weight by a chromatographic method selected from ion exchange and hydrophobic interaction chromatography and removing one immunoglobutin molecule from another immunoglobulin molecule of different binding specificity.

43. An integrated cell culture and purification system for producing a purified cell culture product, consisting essentially of:

a. a cell culture subunit for culturing cells;

b. a purification subunit linked to the cell culture subunit adapted to remove said product from a culture fluid in which the cells are cultured by purification means comprising a solid-phase medium, the solid-phase medium being substantially free of leachables toxic to the cells being cultured; and c. means for circulating said culture fluid from said cell culture subunit to said purification subunit; said cell culture subunit, said purification subunit and said means for circulating being integrated in a single unit and contained in a sterile environment to purify said product in a sterile environment without removing said culture fluid from said integrated cell culture and purification system; said purification subunit separating said product from other molecules of substantially equivalent molecular weight by specific affinity interactions and removing one immunoglobulin molecule from another immunoglobulin molecule of different binding specificity.

44. An integrated cell culture and purification subunit for producing a purified cell culture product, consisting essentially of:

a. a cell culture subunit for culturing cells;

b. a purification subunit linked to the cell culture subunit adapted to remove said product from a culture fluid in which the cells are cultured by purification means comprising a solid-phase medium, the solid-phase medium providing at least one month of continuous cell culture without significant toxic effects on the cells being cultured; and c. means for circulating said culture fluid from said cell culture subunit to said purification subunit; said cell culture subunit, said purification subunit and said means for circulating being integrated in a single unit and contained in a sterile environment to purify said product in a sterile environment without removing said culture fluid from said integrated cell culture and purification system; said purification subunit separating said product from other molecules of substantially equivalent molecular weight by specific affinity interactions and removing one immunoglobulin molecule from another immunoglobulin molecule of different binding specificity.

45. An integrated cell culture and purification system for producing a purified cell culture product, consisting essentially of:

a. a cell culture subunit for culturing cells;

b. a purification subunit linked to the cell culture subunit adapted to remove said product from a culture fluid in which the cells are cultured by purification means comprising a solid-phase medium, the solid-phase medium being substantially free of leachables toxic to the cells being cultured; and c. means for circulating said culture fluid from said cell culture subunit to said purification subunit; said cell culture subunit, said purification subunit and said means for circulating being integrated in a single unit and contained in a sterile environment to purify said product in a sterile environment without removing said culture fluid from said integrated cell culture and purification system; said purification subunit separating said product from other molecules of substantially equivalent molecular weight by a chromatographic method selected from ion exchange and hydrophobic interaction chromatography and removing one immunoglobulin molecule from another immunoglobulin molecule of different binding specificity.

46. An integrated cell culture and purification system for producing a purified cell culture product, consisting essentially of:

a. a cell culture subunit for culturing cells;

b. a purification subunit linked to the cell culture subunit adapted to remove said product from a culture fluid in which the cells are cultured by purification means comprising a solid-phase medium, the solid-phase medium providing at least one month of continuous cell culture without significant toxic effects on the cells being cultured; and c. means for circulating said culture fluid from said cell culture subunit to said purification subunit; said cell culture subunit, said purification subunit, and said means for circulating being integrated in a single unit and contained in a sterile environment to purify said product in a sterile environment without removing said culture fluid from said integrated cell culture and purification system; said purification subunit separating said product from other molecules of substantially equivalent molecular weight by a chromatographic method selected from ion exchange and hydrophobic interaction chromatography and removing one immunoglobulin molecule from another immunoglobulin molecule of different binding specificity.

* * * * *

UNITED STATES PATENT AND TRADEMARK OFFICE
CERTIFICATE OF CORRECTION

PATENT NO. : 5,571,720

DATED : November 5, 1996

INVENTOR(S) : Grandics et al.

It is certified that error appears in the above-identified patent and that said Letters Patent is hereby corrected as shown below:

```
TITLE PAGE:
[76] Inventors, "91006" should read --91007--

[63] Related Data, "1992" should read --1993--

Column 1, line 37, "Would" should read --would--
```

Signed and Sealed this

Fifth Day of August, 1997

*Attest:*

*Attesting Officer*

BRUCE LEHMAN

*Commissioner of Patents and Trademarks*